US007078379B2

(12) United States Patent
Rüegg (10) Patent No.: US 7,078,379 B2
(45) Date of Patent: Jul. 18, 2006

(54) TREATMENT OF CONGENITAL MUSCULAR DYSTROPHIES

(75) Inventor: Markus A. Rüegg, Riehen (CH)

(73) Assignee: Santhera Pharmaceuticals (Schweiz) GmbH, Liestal (CH)

( * ) Notice: Subject to any disclaimer, the term of this patent is extended or adjusted under 35 U.S.C. 154(b) by 270 days.

(21) Appl. No.: 10/161,357

(22) Filed: Jun. 3, 2002

(65) Prior Publication Data

US 2003/0224981 A1    Dec. 4, 2003

(51) Int. Cl.
*A01N 37/18* (2006.01)
*A01N 43/04* (2006.01)
*A61K 38/00* (2006.01)
*A61K 31/70* (2006.01)

(52) U.S. Cl. ............................................ 514/2; 514/44
(58) Field of Classification Search ................ 514/2; 530/350
See application file for complete search history.

(56) References Cited

OTHER PUBLICATIONS

Burgess et al,; "Alternatively Spliced Isoforms of Nerve- and Muscle-derived Agrin: Their Roles at the Neuromuscular Junction," *Neuron*, vol. 23, 33-44 (1999).
Campbell; "Three Muscular Dystrophies: Loss of Cytoskeleton-Extracellular Matrix Linkage," *Cell*, vol. 80, 675-679 (1995).
Denzer et al.; "Agrin Binds to the Nerve-Muscle Basal Lamina via Laminin," *The Journal of Cell Biology*, vol. 137, No. 3, 671-683 (1997).
Denzer et al.; "An Amino-terminal Extension Is Required for the Secretion of Chick Agrin and its Binding to Extracellular Matrix," *The Journal of Cell Biology*, vol. 131, No. 6, 1547-1560 (1995).
Denzer et al.; "Electron microscopic structure of agrin and mapping of its binding site in laminin-1," *The EMBO Journal*, vol. 17 No. 2, 335-343 (1998).
Fox et al.; "Recombinant Nidogen Consists of Three Globular Domains and Mediates Binding of Laminin to Collagen Type IV,"*The EMBO Journal*, vol. 10, No. 11, 3137-3146 (1991).
Gesemann et al.; "Agrin Is a High-affinity Binding Protein of Dystroglycan in Non-muscle Tissue," *The Journal of Biological Chemistry*, vol. 273, No. 1, 600-605 (1998).
Hohenester et al.; "The Crystal Structure of Laminin G-like Module Reveals the Molecular Basis of α-Dystroglycan Binding to Laminins, Perlecan, and Agrin," *Molecular Cell*, vol. 4, 783-792 (1999).
Kohfeldt et al.; "Properties of the Extracellular Calcium Binding Module of the Proteoglycan Testican," *Federation of European Biological Societies*, vol. 414, 557-561 (1997).
Mann et al.; "Amino Acid Sequence of Mouse Nidogen, a Multidomain Basement Membrane Protein with Binding Activity for Laminin, Collagen IV and Cells," *the EMBO Journal*, vol. 8, No. 1, 65-72 (1989).
Mayer et al,; "Absence of Integrin α7 Causes a Novel Form of Muscular Dystrophy," *Nature Genetics*, vol. 17, 318-323 (1997).
Meier et al.; "A Minigene of Neural Agrin Encoding the Laminin-binding and Acetylcholine Receptor-aggregating Domains is Sufficient to induce Postsynaptic Differentation in Muscle Fibres," *European Journal of Neuroscience*, vol. 10, 3141-3152 (1998).
Moll et al.; "An Agrin Minigene Rescues Dystrophic Symptoms in a Mouse Model for Congenital Muscular Dystrophy, " *Nature*, vol. 413, 302-307 (2001).
Noonan et al.; "Identification of cDNA Clones Encoding Different Domains of the Basement Membrane Heparan Sulfate Proteoglycan," *The Journal of Biological Chemistry*, vol. 263, No. 31, 16379-16387 (1988).
Ruegg et al.; "The Agrin Gene Codes for a Family of Basal Lamina Proteins That Differ in Function and Distribution," *Neuron*, vol. 8, 691-699, (1992).
Ruegg et al.; "Agrin orchestrates synaptic differentiation at the vertebrate neuromuscular junction," *TINS*, vol. 21, No. 1, 22-27 (1998).
Sugita et al,; "A Stoichiometric Complex of Neurexins and Dystroglycan in Brain," *The Journal of Cell Biology*, vol. 154, No. 2, 435-445 (2001).
Talks et al,; "Binding of the G domains of laminin α1 and α2 chains and perlecan to heparin, sulfatides, α-dystroglycan and several extracellular matrix proteins," *The EMBO Journal*, vol. 18, No. 4, 863-870 (1999).
Talts et al,; "Structual Analysis and Proteolytic Processing of Recombinant G Domain of Mouse Laminin α2 Chain," *Federation of European Biochemical Societies*, vol. 426, 71-76 (1998).

*Primary Examiner*—Robert S. Landsman
(74) *Attorney, Agent, or Firm*—Leydig, Voit & Mayer, Ltd.

(57) ABSTRACT

The invention provides a method of treating congenital muscular dystrophy due to a mutation in the LAMA2 gene in a mammal. The method comprises administering to the mammal a therapeutically effective amount of a protein comprising at least one binding domain for a laminin, at least one binding domain for α-dystroglycan, and at least one follastatin-like domain.

8 Claims, 2 Drawing Sheets

Agrin-Perlecan-Plasmid

Fig. 2b

Nidogen-Agrin-Plasmid

Fig. 2c

Agrin-Nidogen-Plasmid

TREATMENT OF CONGENITAL MUSCULAR DYSTROPHIES

TECHNICAL FIELD OF THE INVENTION

The present invention relates to a method of treating congenital muscular dystrophy in a mammal involving the administration of a protein comprising at least one binding domain for a laminin and at least one binding domain for α-dystroglycan or a substance that upregulates endogenous agrin, proteins and nucleic acids for use in the method, a composition comprising the protein or nucleic acid, a non-human transgenic animal expressing the protein, and a method of identifying a substance that upregulates endogenous agrin in a mammal.

BACKGROUND OF THE INVENTION

A large number of medical disorders are due to genetic defects that result in the expression of mutated and malfunctioning proteins or even total absence of that protein. Diseases, such as dystrophinopathies (e.g., Duchenne and Becker muscular dystrophies), sarcoglycanopathies, and laminin or collagen deficiencies, affect the body muscle mass and can be considered disorders, for which replacement of the malfunctioning or absent protein could effect treatment.

Congenital muscular dystrophy is a specific example of these genetically based disorders. It is a heterogeneous and severe, progressive muscle-wasting disease that frequently leads to death in early childhood (Tome et al., in *Neuromuscular Disorders: Clinical and Molecular Genetics* (ed., Emery), pp. 21–57 (John Wiley & Sons, West Sussex (1998)); and Miyagoe-Suzuki et al., *Microsc. Res. Tech.* 48: 181–191 (2000)). Most cases of congenital muscular dystrophy are caused by mutations in LAMA2, the gene encoding the α2 chain of the main laminin isoforms expressed by muscle fibers. Muscle fiber deterioration in this disease is thought to be caused by failure to form the primary laminin scaffold, which is necessary for basement membrane structure (Colognato et al., *Dev. Dyn.* 218: 213–234 (2000)), and the missing interaction between muscle basement membrane and the dystrophin-glycoprotein complex (DGC) (Campbell, *Cell* 80: 675–679 (1995)) or the integrins (Mayer et al., *Nature Genet.* 17: 318–323 (1997)).

Figure 1A:
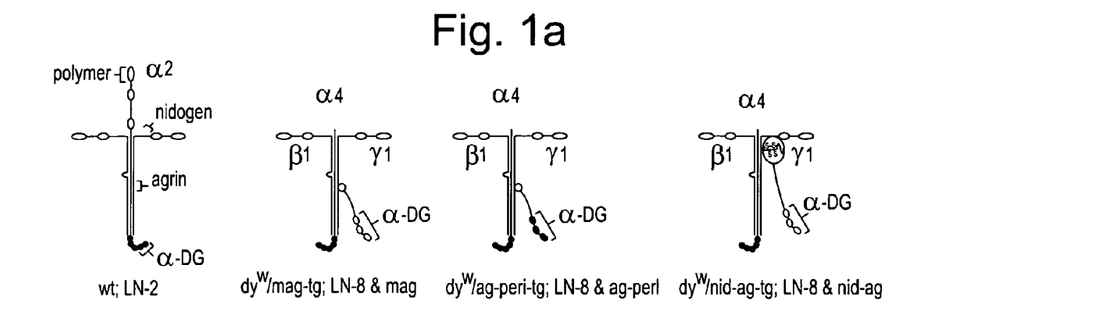
FIG. 1b is a schematic representation of the chick agrin cDNA and the mini-agrin cDNA construct used in the animal model of the Examples in which "NtA" indicates the laminin-binding module, "FS" indicates the follistatin-like module, and "MCK" indicates the muscle creatine kinase promoter, and in which the agrin domains are labeled in accordance with Ruegg, *Trends Neurosci.* 21: 22–27 (1998)).
FIG. 1c is a schematic representation of the generation of the agrin-perlecan chimeric construct.
FIG. 1d is a schematic representation of the nidogen-agrin chimeric construct.

Laminins are cross-shaped heterotrimers of α, β, and γ chains (see FIG. 1a). The five α, three β, and three γ chains give rise to at least twelve different protein isoforms (laminin-1 to laminin-12) (Colognato (2000), supra), which differ in their tissue distribution (Patton et al, *J. Cell Biol.* 139: 1507–1521 (1997)). Mutations in the laminin α2 chain, which is the most predominant α chain in muscle and peripheral nerve, cause a most severe form of congenital muscular dystrophy, commonly referred to as merosin-deficient congenital muscular dystrophy (MCMD). Hallmarks of MCMD are a complete or partial loss of structured muscle basement membrane, ongoing muscle necrosis (which results in elevated levels of creatine kinase (CK) in the blood) and demyelination of peripheral nerves (Tome (1998), supra; Miyagoe-Suzuki (2000), supra). Deficiency of laminin α2 is accompanied by upregulation of the laminin α4 chain, giving rise to laminin-8 (see FIG. 1a; Patton (1997), supra; and Ringelmann, *Exp. Cell Res.* 246: 165–182 (1999)). This α chain, however, lacks domains important for laminin polymerization (Colognato (2000), supra) and binds only weakly to α-dystroglycan (Talts et al., *J. Biol. Chem.* 275: 35192–35199 (2000)), a principal receptor for the α2 chain (see FIG. 1a).

In view of the above, there is a need for the treatment of disorders based on genetic defects that result in malfunctioning proteins or the total absence of proteins. In particular, there is a need for treating congenital muscular dystrophy by compensating for the lack of the physical stability of muscle fibers and thereby restoring muscle function. The present invention provides such a treatment. This and other objects of the present invention, as well as additional inventive features, will be apparent from the detailed description provided herein.

BRIEF SUMMARY OF THE INVENTION

The present invention provides methods of treating congenital muscular dystrophy in a mammal. One method comprises administering to the mammal a therapeutically effective amount of a protein or polypeptide comprising at least one binding domain for a laminin and at least one binding domain for α-dystroglycan, whereupon the mammal is treated for congenital muscular dystrophy. The other method comprises administering to the mammal a therapeutically effective amount of a substance that upregulates endogenous agrin, whereupon the mammal is treated for congenital muscular dystrophy.

The present invention further provides an isolated and purified non-naturally occurring protein or polypeptide comprising at least one binding domain for a laminin and at least one binding domain for α-dystroglycan. In this regard, an isolated and purified nucleic acid encoding the protein or polypeptide, optionally in the form of a recombinant vector, is also provided.

In view of the foregoing, the present invention also provides a composition comprising the above-described protein or polypeptide and a pharmaceutically acceptable carrier. Similarly provided is a composition comprising the above-described nucleic acid and a pharmaeutically acceptable carrier.

A nonhuman transgenic animal, which expresses the above-described protein or polypeptide is also provided. Likewise, a nonhuman transgenic animal, which comprises and expresses the above-described nucleic acid, is provided.

Still further provided by the present invention is a method of identifying a substance that upregulates endogenous agrin in a mammal. The method comprises:

(i) contacting a mammalian muscle or cells or tissue thereof with a substance, and (ii) comparing the amount of agrin in the mammalian muscle or cells or tissue thereof in the presence of the substance with (a) the amount of agrin in the mammalian muscle or cells or tissue thereof before contact with the substance or (b) the amount of agrin in a mammalian muscle or cells or tissue thereof in the absence of the substance, whereupon an increase in the amount of agrin in the mammalian muscle or cells or tissue thereof in the presence of the substance as compared to (a) or (b) indicates that the substance upregulates endogenous agrin in a mammal.

BRIEF DESCRIPTION OF THE FIGURES

FIG. 1a is a schematic representation of laminins from different mouse genotypes in which "wt" indicates wild-type, "$dy^W$" indicates genotype deficient in the laminin α2 chain, "$dy^W$/mag-tg" indicates heterozygous genotype $dy^W$/mini-agrin transgenic, "ag-perl-tg" indicates agrin-perlecan transgenic (the α-dystroglycan-binding portion of the mini-agrin construct is replaced with that of perlecan), "dy$^W$/ag-perl-tg" indicates heterozygous genotype dy$^W$/ag-perl-tg, "nid-ag-tg" indicates nidogen-agrin transgenic (the laminin-binding domain of the mini-agrin construct is replaced with the G3 domain of nidogen that binds to the laminin γ1 chain), "dy$^W$/nid-ag-tg" indicates heterozygous genotype dy$^W$/nid-ag-tg, "α2" indicates the laminin α2 chain, "α4" indicates the laminin α4 chain, "β1" indicates the β1 chain of laminin, "γ1" indicates the γ1 chain of laminin, "LN-2" indicates the isoform laminin-2, "LN-8" indicates the isoform laminin-8, "polymer" indicates the region in the α2 chain of laminin necessary for polymerization, "nidogen" indicates the region in the α2 chain of laminin necessary for binding to nidogen, "agrin" indicates the region in the α2 chain of laminin necessary for binding to agrin, "α-DG" indicates the region in the α2 chain of laminin necessary for binding to α-dystroglycan, and "mag" indicates mini-agrin.

DETAILED DESCRIPTION OF THE PRESENT INVENTION

The present invention is predicated, at least in part, on the surprising and unexpected discovery that a genetic disorder can be treated by the administration of a protein, which is functionally equivalent to the disease-causing protein but which shows weak homology at the amino acid level. In view of this discovery, the present invention provides methods of treating congenital muscular dystrophy in a mammal. By "treating" is meant the slowing, interrupting, arresting or stopping of the progression of the disease or condition based on a genetic defect and does not necessarily require the complete elimination of all disease symptoms and signs. "Treating" is intended, however, to include the prophylaxis of the disease or condition, wherein "prophylaxis" is understood to be any degree of inhibition of the time of onset or severity of signs or symptoms of the disease or condition, including, but not limited to, the complete prevention of the disease or condition.

One method comprises administering to the mammal a therapeutically effective amount of a protein or polypeptide comprising at least one binding domain for a laminin and at least one binding domain for α-dystroglycan, whereupon the mammal is treated for congenital muscular dystrophy. While the mammal can be a guinea pig, dog, cat, rat, mouse, horse, cow, sheep, monkey or chimpanzee, preferably, the mammal is a human, and the congenital muscular dystrophy is due to a mutation in the LAMA2 gene.

Preferably, the at least one binding domain for a laminin is, the at least one binding domain for α-dystroglycan is, or both of the at least one binding domain for a laminin and the at least one binding domain for α-dystroglycan are derived from an extracellular matrix protein, which can be the same or different. The term "derived from" means that the amino acid sequence of the binding domain is preferably at least 50%, more preferably at least 80%, and most preferably at least 90% identical to the binding domain of the naturally occurring, fully functional, i.e., wild-type, protein, and retains at least some, preferably at least 20%, more preferably at least 50%, and most preferably at least 90% of the specific binding function of the binding domain of the wild-type protein or functional fragment thereof. Thus, the binding domain can be a functional derivative of the wild-type binding domain, such as a functional fragment, variant (e.g., structurally and functionally similar to the wild-type protein and has at least one functionally equivalent domain), analog (e.g., a protein or fragment thereof substantially similar in function to the wild-type protein or fragment thereof), chemical derivative (e.g., contains additional chemical moieties, such as polyethyleneglycol and derivatives thereof), or peptidomimetic (e.g., a low molecular weight compound that mimics a peptide in structure and/or function (see, e.g., Abell, *Advances in Amino Acid Mimetics and Peptidomimetics*, London: JAI Press (1997); Gante, *Peptidmimetica—massgeschneiderte Enzyminhibitoren Angew. Chem.* 106: 1780–1802 (1994); and Olson et al., *J. Med. Chem.* 36: 3039–3049 (1993)) of the wild-type binding domain or functional fragment thereof. The design of the protein or polypeptide is based on functional, not structural, similarity between the mutated malfunctioning host protein, such as the laminin α2 protein, and the therapeutic protein. Binding domains from extracellular matrix proteins from the same species of mammal are less likely to result in unwanted immune responses and are, therefore, preferred sources for such binding domains. Preferably, the extracellular matrix protein is agrin (Gesemann et al., *J. Biol. Chem.* 273: 600–605 (1998)), nidogen (Fox et al., *EMBO J.* 10: 1337–1346 (1991)), laminin 2 (Talts et al., *EMBO J.* 18: 863–870 (1999)), perlecan (Hohenester et al., *Mol. Cell* 4: 783–792 (1999)), or a neurexin (Sugita et al., *J. Cell Biol.* 154: 435–445 (2001)).

In one preferred embodiment, the at least one binding domain for a laminin and the at least one binding domain for α-dystroglycan are derived from agrin. In another preferred embodiment, the at least one binding domain for a laminin is derived from nidogen and the at least one binding domain for α-dystroglycan is derived from agrin. In yet another preferred embodiment, the at least one binding domain for a laminin is derived from agrin and the at least one binding domain for α-dystroglycan is derived from perlecan. Examples of suitable domains for use in the context of the present invention include domain G3 of nidogen (base pairs 2,554–3,756; amino acids 845–1,245; GenBank X14480 (mouse)), domain V of perlecan (base pairs 9,518–11,699; amino acids 2,977–3,707; GenBank NM008305 (mouse)), domains NtA and follistatin-like domain (FSI) of agrin (base pairs 1–759 (numbering of nucleotides according to assembled sequence; initiation of translation (ATG) was defined as nucleotide 1, which is nucleotide 91 in GenBank U35613); amino acids 1–253; GenBank U35613 and M94271 (chick)); and domains FSI and C95 of agrin (base pairs 517–6249 (numbering of nucleotides according to assembled sequence; initiation of translation (ATG) was defined as nucleotide 1, which is nucleotide 91 in GenBank U35613); amino acids 173–2083; GenBank U35613 and M94271 (chick)).

Figure 2A:
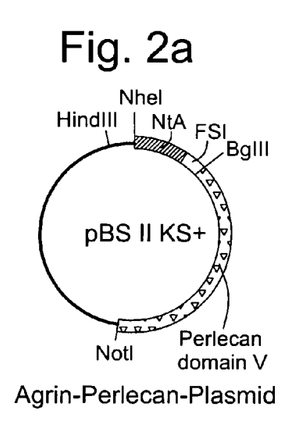
FIG. 2a is a schematic representation of the plasmid encoding the agrin-perlecan chimera.
Figure 2B:
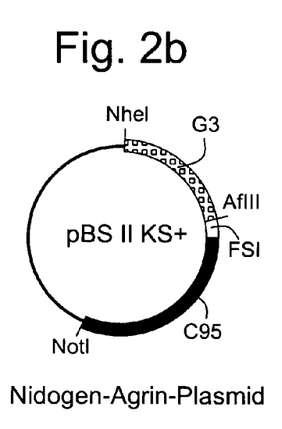
FIG. 2b is a schematic representation of the plasmid encoding the nidogen-agrin chimera.
Figure 2C:
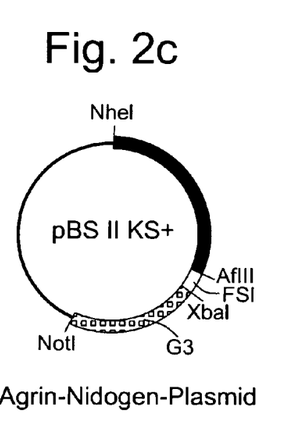
FIG. 2c is a schematic representation of the plasmid encoding the agrin-nidogen chimera.

Domains can be amplified by PCR using specific primers in combination with plasmid templates encoding the cDNA of nidogen (Mann et al. *EMBO J.* 8: 65–72 (1989); GenBank X14480), perlecan (Noonan et al., *J. Biol. Chem.* 263: 16379–16387 (1988); GenBank NM008305), and chick agrin (Denzer et al., *J. Cell Biol.* 131: 1547–1560 (1995); GenBank U35613; Ruegg et al., *Neuron* 11: 691–699 (1992); GenBank M94271). The PCR products can be inserted into a suitable vector, such as the BS II KS+ vector, using standard cloning technologies, resulting in the vectors of FIG. 2a–FIG. 2c, for example. The agrin-perlecan construct (FIG. 2a) was generated and digested with Hin dIII-Not I and inserted into the C-His pCEP-PU vector. This vector is derived essentially by exchanging the resistance gene for hygromycin with a resistance gene for puromycin in the pCEP-SH3 vector (Invitrogen, Inc.). The vector also contains a His-tag motif at the carboxy-terminal region of the multiple cloning site (Kohfeldt et al., *FEBS Lett.* 414: 557–561 (1997)). Of the nidogen-agrin constructs, one combines the G3-domain of nidogen with the first FSI and the C95 domain of agrin (see FIG. 2b), and the other combines the C95 domain and the FSI of agrin with the G3 domain of nidogen (see FIG. 2c). Both chimeric constructs were digested with Nhe I-Not I and inserted into the C-His pCEP-PU vector, in order to have the BM-40 as signal sequence of the vector. This His-Tag of the pCEP-PU vector was in frame for all three constructs. Upon expression in HEK 293 EBNA cells (Talts et al., *FEBS Lett.* 426: 71–76 (1998)) and purification, the binding activity of these chimeric proteins was confirmed using ELISA technology as described (Denzer et al., *J. Cell Biol.* 137: 671–683 (1997)). For expression in a mammal, such as a transgenic mouse, the constructs can be expressed in alternative vectors that make use of promoters such as the muscle creatine kinase (MCK) promoter, the cytomegalovirus (CMV) promoter, a tetracycline-regulatable promoter, or a doxycycline-regulatable promoter.

The protein or polypeptide can be administered by any suitable route of administration as known in the art, such as orally, e.g., in the form of a tablet or capsule, subcutaneously, transdermally, rectally, intravenously, parenterally, e.g., by injection and the like. Preferably, the protein is administered by intramuscular injection. Alternatively, the protein or polypeptide can be administered by the administration of an isolated and purified nucleic acid encoding and expressing the protein or polypeptide. Suitable routes of administering nucleic acids are also known in the art. Preferably, the isolated and purified nucleic acid encoding and expressing the protein or polypeptide is administered by intramuscular injection. One of ordinary skill in the art will readily appreciate that one route may have a more immediate effect than another route.

Preferably, the isolated and purified nucleic acid is in the form of a recombinant vector, such as a viral vector. The selection of a suitable vector and expression control sequences as well as vector construction are within the ordinary skill in the art. Preferably, the viral vector is an adenoviral vector, an adeno-associated viral vector, a retroviral vector, a Herpes simplex viral vector, a lentiviral vector, a Sindbis viral vector, or a Semliki forest viral vector. Preferably, the isolated and purified nucleic acid encoding and expressing the protein or polypeptide is operably linked to the MCK promoter, the CMV promoter, a tetracycline-regulatable promoter, or a doxycycline-regulatable promoter. In the case of agrin, high efficiency viral vector transfection may not be required because mini-agrin is secreted from muscle fibers and can act on neighboring, non-transfected fibers.

Generally, to ensure effective transfer of the vectors of the present invention, it is preferred that about 1 to about 5,000 copies of the vector according to the invention be employed per cell to be contacted, based on an approximate number of cells to be contacted in view of the given route of administration, and it is even more preferred that about 3 to about 300 pfu enter each cell. However, this is merely a general guideline, which by no means precludes use of a higher or lower amount, as might be warranted in a particular application, either in vitro or in vivo. The actual dose and schedule can vary depending on whether the composition is administered in combination with other compositions, e.g., pharmaceutical compositions, or depending on interindividual differences in pharmacokinetics, drug disposition, and metabolism. Similarly, amounts can vary in in vitro applications depending on the particular type of cell or the means by which the vector is transferred. One skilled in the art easily can make any necessary adjustments in accordance with the necessities of the particular situation.

Another method of treating congenital muscular dystrophy in a mammal comprises administering to the mammal a therapeutically effective amount of a substance that upregulates endogenous agrin, whereupon the mammal is treated for congenital muscular dystrophy. Preferably, the substance that upregulates endogenous agrin is agrin, such as any of the known isoforms of agrin (Ruegg (1992), supra). Other substances that upregulate endogenous agrin can be identified in accordance with the methods described herein. A therapeutically effective amount of a substance that upregulates endogenous agrin is any amount that results in an increase in the amount of endogenous agrin. Such an amount can range from 1 mg to 1,000 mg/kg body weight and can be determined routinely in accordance with dosage range-finding techniques known to those of ordinary skill in the art.

In view of the above, the present invention further provides an isolated and purified non-naturally occurring protein or polypeptide comprising at least one binding domain for a laminin and at least one binding domain for α-dystroglycan. Preferably, the at least one binding domain for a laminin is, the at least one binding domain for α-dystroglycan is, or both of the at least one binding domain for a laminin and the at least one binding domain for α-dystroglycan are derived from an extracellular matrix protein, which can be the same or different. Preferably, the extracellular matrix protein is agrin, nidogen, laminin 2, perlecan, or a neurexin. In a preferred embodiment, the at least one binding domain for a laminin and the at least one binding domain for α-dystroglycan are derived from agrin. In another preferred embodiment, the at least one binding domain for a laminin is derived from nidogen and the at least one binding domain for α-dystroglycan is derived from agrin. In yet another preferred embodiment, the at least one binding domain for a laminin is derived from agrin and the at least one binding domain for α-dystroglycan is derived from perlecan. It is preferred that the at least one binding domain for a laminin and/or the at least one binding domain for α-dystroglycan are derived from human proteins. More preferably, both of the at least one binding domain for a laminin and the at least one binding domain for α-dystroglycan are derived from human proteins.

Also in view of the above, the present invention provides an isolated and purified nucleic acid encoding the above-described protein or polypeptide, optionally in the form of a recombinant viral vector. Suitable vectors are reviewed in Kay et al., *Nature Medicine* 7: 33–40 (2001); Somia et al., *Nature Reviews* 1: 91–99 (2000); and van Deutekom et al., *Neuromuscular Disorders* 8: 135–148 (1998). Preferably, the viral vector is an adenoviral vector (preferred examples are described in Acsadi et al., *Hum. Gene Ther.* 7(2): 129–140 (1996); Quantin et al., *PNAS USA* 89(7): 2581–2584 (1992); and Ragot et al., *Nature* 361 (6413): 647–650 (1993)), an adeno-associated viral vector (preferred examples are described in Rabinowitz et al., *Curr. Opin. Biotechnol.* 9(5): 470–475 (1998)), a retroviral vector preferred examples are described in Federico, *Curr. Opin. Biotechnol.* 10(5): 448–453 (1999)), a Herpes simplex viral vector (see, e.g., Latchman, Gene 264(1): 1–9 (2001)), a lentiviral vector, a Sindbis viral vector, or a Semliki forest viral vector. Suitable promoters for operable linkage to the isolated and purified nucleic acid are known in the art. Preferably, the isolated and purified nucleic acid encoding the protein is operably linked to a promoter selected from the group consisting of the muscle creatine kinase (MCK) promoter (Jaynes et al., *Mol. Cell Biol.* 6: 2855–2864 (1986)), the cytomegalovirus (CMV) promoter, a tetracycline-regulatable promoter (Gossen et al., *PNAS USA* 89: 5547–5551 (1992)), and a doxycycline-regulatable promoter (Gossen et al. (1992), supra). Vector construction, including the operable linkage of a coding sequence with a promoter and other expression control sequences, is within the ordinary skill in the art.

A composition comprising (i) the above-described protein or polypeptide or nucleic acid and (ii) a pharmaceutically acceptable carrier (or excipient) is also provided. Suitable carriers or excipients are well-known in the art. A carrier or excipient can be a solid, semi-solid or liquid material, which can serve as a vehicle or medium for the active ingredient. One of ordinary skill in the art in the field of preparing compositions can readily select the proper form and mode of administration depending upon the particular characteristics of the product selected, the disease or condition to be treated, the stage of the disease or condition, and other relevant circumstances (*Remington's Pharmaceutical Sciences*, Mack Publishing Co. (1990)). The proportion and nature of the pharmaceutically acceptable carrier or excipient are determined by the solubility and chemical properties of the protein or nucleic acid selected, the chosen route of administration, and standard pharmaceutical practice. The pharmaceutical preparation may be adapted for oral, parenteral or topical use and may be administered to the patient in the form of tablets, capsules, suppositories, solution, suspensions, or the like. The proteins and nucleic acids of the present invention, while effective themselves, can be formulated and administered in the form of their pharmaceutically acceptable salts, such as acid addition salts or base addition salts, for purposes of stability, convenience of crystallization, increased solubility, and the like.

Further provided is a nonhuman transgenic animal, which expresses the above-described protein or polypeptide, such as from an above-described nucleic acid. Preferably, the animal is a mouse, a rat, a hamster, a guinea pig, a swine, a cad, a dog, or a monkey. Similarly provided are transgenic cells, preferably muscle cells, which express the above-described protein or polypeptide, such as from an above-described nucleic acid. Methods of producing transgenic cells and transgenic animals are within the ordinary skill in the art.

Still further provided is a method of identifying a substance that upregulates endogenous agrin in a mammal. The method comprises:

(i) contacting a mammalian muscle or cells or tissue thereof with a substance, and (ii) comparing the amount of agrin in the mammalian muscle or cells or tissue thereof in the presence of the substance with (a) the amount of agrin in the mammalian muscle or cells or tissue thereof before contact with the substance or (b) the amount of agrin in a mammalian muscle or cells or tissue thereof in the absence of the substance, whereupon an increase in the amount of agrin in the mammalian muscle or cells or tissue thereof in the presence of the substance as compared to (a) or (b) indicates that the substance upregulates endogenous agrin in a mammal. Preferably, the endogenous agrin is any of the known isoforms of agrin.

The mammalian muscle (or cells or tissues thereof) is preferably removed from a mammal and maintained under suitable laboratory conditions. Any suitable method of contacting the muscle with the substance to be tested can be employed. The determination of the amount of agrin in the muscle can be determined in accordance with standard laboratory methods, such as those employed in the Examples herein. Methods employed to compare levels of agrin are standard in the art and include those employed in the Examples herein.

EXAMPLES

The following examples serve to illustrate further the present invention and are not intended to limits its scope in any way.

Example 1

This example demonstrates that it is possible to restore muscle function in a mouse model of congenital muscular dystrophy in accordance with the present inventive method.

The heparan sulfate proteoglycan agrin is best known for its activity to induce postsynaptic specializations at the neuromuscular junction (NMJ; reviewed in Ruegg et al. (1998), supra; and Burgess et al., *Neuron* 23: 33–44 (1999)). Alternative mRNA splicing generates protein isoforms that differ in their activity to induce postsynaptic differentiation.

Figure 1B:
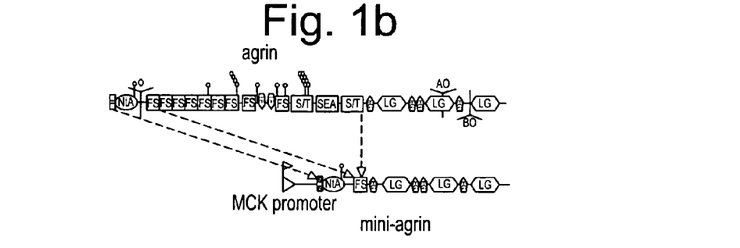
Figure 1C:
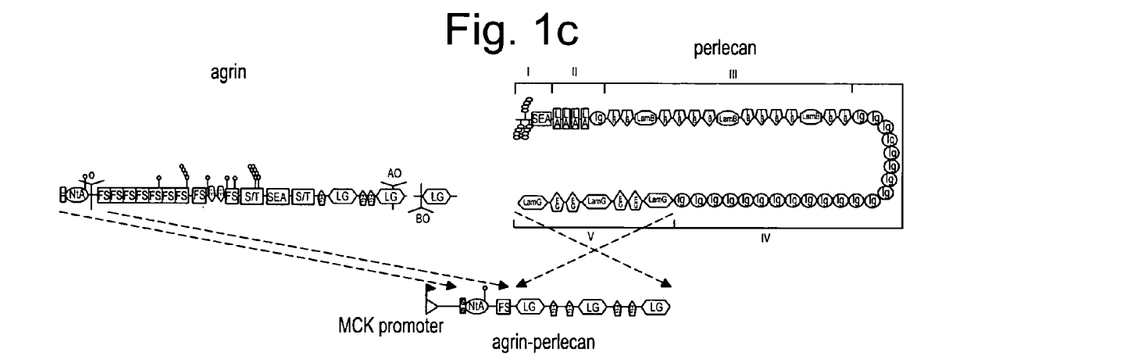
Figure 1D:
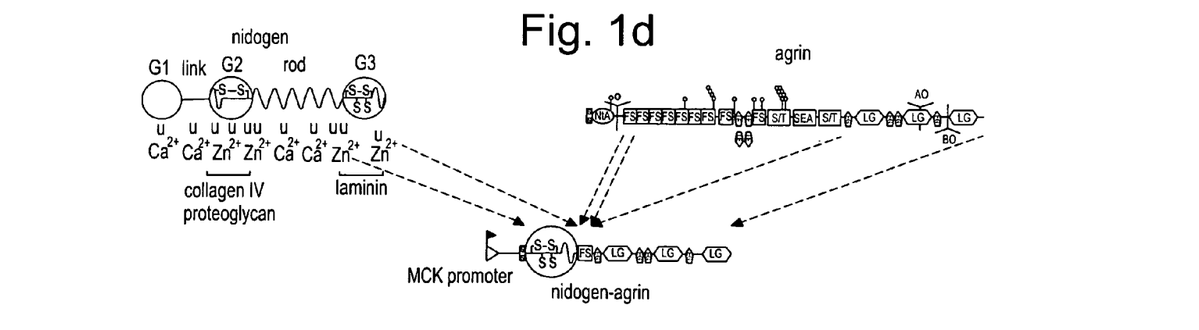

A chick muscle agrin-minigene was prepared in a manner analogous to that used to prepare a neural agrin-minigene (Meier et al., *Eur. J. Neurosci.* 10:3141–3152 (1998)) by combining the amino-terminal agrin (NtA in Denzer et al., *EMBO J.* 17: 335–343 (1998)) domain, which binds laminins (Denzer et al., *J. Cell Biol.* 137: 671–683 (1997); and Denzer et al. (1998), supra), the first follistatin-like domain, and the α-dystroglycan binding domain (Gesemann et al., *J. Biol. Chem.* 273: 600–605 (1998)) and placing the combined sequences under the control of the mouse MCK promoter as described in Jaynes et al., *Mol. Cell Biol.* 6: 2855–2864 (1986), and Sternberg et al., *Mol. Cell Biol.* 8: 2896–2909 (1988), and as shown in FIG. 1*b*. FIG. 1*b* is a schematic representation of chick agrin and the mini-agrin in which "NtA" indicates the laminin-binding module, "FS" indicates the follistatin-like module, and "MCK" indicates the muscle creatine kinase promoter, and in which the agrain domains are labeled in accordance with Ruegg (1998), supra. Restriction enzymes used to excise the cDNA construct are indicated. These domains are preferably derived from a chick or a mouse and more preferably derived from a human.

The construct was injected into mouse oocytes. Transgenic lines were identified by PCR and Southern blot analysis using primers and probes from the 3'-untranslated region of chick agrin mRNA. From eight transgenic founders, two lines were used that expressed the mini-agrin protein at high levels. Mice expressing the chick muscle agrin-minigene were then bred with animals carrying a null mutation in the lama2 gene (dy$^W$ in Kuang et al. (1998), supra).

FIG. 1a is a schematic representation of laminins from different mouse genotypes in which "wt" indicates wild-type, "dy$^W$" indicates genotype deficient in the laminin α2 chain, "dy$^W$/mag-tg" indicates heterozygous genotype dy$^W$/mini-agrin transgenic, "ag-perl-tg" indicates agrin-perlecan transgenic (the α-dystroglycan-binding portion of the mini-agrin construct is replaced with that of perlecan), "dy$^W$/ag-perl-tg" indicates heterozygous genotype dy$^W$/ag-perl-tg, "nid-ag-tg" indicates nidogen-agrin transgenic (the laminin-binding domain of the mini-agrin construct is replaced with the G3 domain of nidogen that binds to the laminin γ1 chain), "dy$^W$/nid-ag-tg" indicates heterozygous genotype dy$^W$/nid-ag-tg, "α2" indicates the laminin α2 chain, "α4" indicates the laminin α4 chain, "β1" indicates the β1 chain of laminin "γ1" indicates the γ1 chain of laminin, "LN-2" indicates the isoform laminin-2, "LN-8"indicates the isoform laminin-8, "polymer" indicates the region in the α2 chain of laminin necessary for polymerization, "nidogen" indicates the region in the α2 chain of laminin necessary for binding to nidogen, "agrin" indicates the region in the α2 chain of laminin necessary for binding to agrin, "α-DG" indicates the region in the α2 chain of laminin necessary for binding to α-dystroglycan, and "mag" indicates mini-agrin. Genotyping of dy$^W$ mice was done as described in Kuang et al. (*J. Clin. Invest.* 102: 844–852 (1998)). Homozygous dy$^W$ mice show the same pathology as the spontaneous lama2-mutant mice (dy), which are the classical animal model for MCMD (Sunada et al. *J. Biol. Chem.* 269: 13729–13732 (1994); and Xu et al. *Nature Genet.* 8: 297–302 (1994)).

Muscle basement membranes of wild-type mice contain high amounts of laminin-2. In mice deficient of the laminin α2 chain (dy$^W$), the homologous laminin α4 chain is upregulated (Patton, (1997), supra; Ringelmann (1999), supra) and combines with the β1 and the γ1 chain to laminin-8. The laminin α4 chain is truncated at the amino-terminus and binds only weakly to α-dystroglycan (Talts (2000), supra).

For immunoblots muscles were rapidly homogenized in 1 ml extraction buffer (75 mM Tris-HCl, pH 6.8; 3.8% SDS; 4 M urea; 20% glycerol; 5% β-mercaptoethanol). After protein denaturation (95° C. for 5 min), non-dissolved protein was removed by centrifugation (14,000 g for 5 min). Fifty μg protein, as determined by Lowry protein assay, were loaded onto each lane, separated on a 3–12% SDS-PAGE and immunoblotted. The transgenic mini-agrin protein appeared as a doublet of ~120K and 105K, respectively, where the smaller band probably represents a proteolytic breakdown product.

In transgenic wild-type (mag-tg) and laminin α2-deficient mice (dy$^W$/mag-tg) the mini-agrin is expressed in skeletal muscle, but only little is expressed in heart. In laminin α2-deficient mice (dy$^W$), no agrin-specific immunoreactivity was detected. Anti-chick agrin antibodies stained the entire muscle fiber circumference in mag-tg and dy$^W$/mag-tg, but not in dy$^W$ or wild-type, mice. Chick agrin-like immunoreactivity only partially overlapped with acetylcholine receptors, but co-distributed with the laminin α2 chain, indicating that the mini-agrin protein is an integral part of the muscle basement membrane. The staining pattern of the transgenic agrin protein was similar in all muscles examined, which included extensor digitorum longus, soleus, diaphragm, and intercostal muscle.

In 16 week-old mice, which is at an age when most of the laminin α2-deficient mice had died already, signs of a mild myopathy were observed in transgenic crossbreeds of agrin mini-gene-expressing, laminin α2-deficient mice (dy$^W$/mag-tg mice). The mini-agrin, which binds to laminin-8 (Denzer et al. (1997), supra; and Denzer et al. (1998), supra) and α-dystroglycan (Gesemann (1998), supra), restored linkage of muscle basement membrane and the muscle cell, thereby compensating for the loss of the laminin α2 chain in deficient mice. This demonstrates that the mini-agrin rescued most of the muscle degeneration. The remaining pathology in transgenic crossbreeds of agrin mini-gene-expressing, laminin α2-deficient mice, such as hindlimb paralysis and cardio-myopathy, also may be caused by the lack of mini-agrin expression in the respective tissue, i.e., heart and peripheral nerve, as compared to skeletal muscle, where expression of the mini-agrin was high. The data indicate that substantial amelioration of the myopathy in these mice involves stabilization of α-dystroglycan.

Example 2

This example describes the comparative health of wild-type, mini-agrin-treated, and untreated dystrophic mice.

As reported earlier (Kuang (1998), supra), dy$^W$ mice appear much more passive, smaller and thinner than wild-type mice. The overall health of dy$^W$/mag-tg mice was greatly improved compared to their dy$^W$ littermates. Weight gain and growth curves, which are greatly delayed in dy$^W$ mice, were similar for dy$^W$/mag-tg and wild-type mice. The beneficial influence of the mini-agrin also became apparent in the locomotory activity of the mice.

Locomotion was examined in an open field test by placing mice into a new cage and measuring (by videotape and manual measurement) the time spent walking around in the first 5 minutes. Wild-type mice spent more than 90% of the time in motion, while dy$^W$ mice spent less than 20% of the time moving. This striking inertia was not seen in dy$^W$/mag-tg mice.

Similar results were also apparent in a rotating rod (rotarod) test. In the rotarod task, animals were first trained 3 times to allow accommodation to the task. After resting for at least 1 hr, animals were tested with the rod turning at 16 rpm. Each mouse was tested three times for 2 min. When possible, the data were collected blindly.

There, dy$^W$ mice fell from the rotarod instantaneously, while most dy$^W$/mag-tg mice managed to stay. The beginning of partial hindleg paralysis in dy$^W$/mag-tg mice is likely the reason for their weaker performance compared to wild-type mice. This partial loss of motor control in dy$^W$/mag-tg mice is due to progressive demyelination of peripheral nerves (Kuang (1998), supra), a phenotype that is not rescued because the mini-agrin transgene is not expressed in peripheral nerves. Expression of the agrin transgene also had a strong impact on the longevity of the mice. On average, dy$^W$ mice died at the age of 8 weeks and dy$^W$/mag-tg mice died around 40 weeks.

Example 3

This example compares muscle cell pathology in wild-type mice, mini-agrin-treated and untreated dystrophic mice.

Different muscles from 4 week-old mice were immersed in 7% gum tragacanth (Sigma Chemical Co., St. Louis, Mo.), rapidly frozen in liquid nitrogen-cooled isopentane, sliced into 10 μm thick sections, and examined by hematoxylin & eosin (H&E) staining. All of the hallmarks of MCMD were observed in $dy^W$ mice, such as extensive degeneration and some regeneration of muscle fibers and an accompanied expansion of connective tissue. In contrast, no degeneration was apparent in $dy^W$ mice that expressed the mini-agrin.

A typical sign of the ongoing degeneration and regeneration of muscle fibers is a variation in the fiber size (Tome (1998), supra). Muscle fibers from each different genotype of mice were sectioned and digitized. The number of squares (8×8 μm) was counted per muscle fiber. In addition, the relative percentage of types of fibers was determined for each genotype. A high percentage of very small (up to 1,300 μm$^2$) and some very large muscle fibers (>3,900 μm$^2$; Miyagoe-Suzuki (2000), supra) were indeed found in $dy^W$ mice. In contrast, $dy^W$/mag-tg mice displayed a more uniform fiber size distribution that was indistinguishable from wild-type mice.

The ongoing muscle necrosis was also manifested by the more than 8-times higher creatine kinase (CK) levels in blood collected from the tails of 4 week-old $dy^W$ mice. In $dy^W$ mice expressing the mini-agrin ($dy^W$/mag-tg), CK activity was more than 2 times lower, but remained approximately 3 times higher than in wild-type mice. Interestingly, the CK activity is also approximately 3 times elevated in the blood of $dy^W$ mice that express a transgene of the human laminin α2 chain (Kuang (1998), supra), which is expected to rescue fully muscle pathology. Thus, the still elevated CK levels in $dy^W$/mag-tg mice may originate from heart muscle, from changes caused by the demyelination of peripheral nerves, or from residual myopathy not fully rescued by the mini-agrin transgene.

To investigate this, H&E-stained muscle cross-sections of 16 week-old mice were examined. The few $dy^W$ mice that survived for 16 weeks showed signs of a chronic and severe degenerative myopathy. In these animals, fibrous and fatty tissue had replaced a high percentage of the muscle and most of the remaining fibers were round and small. In contrast, most of the muscle fibers in $dy^W$/mag-tg mice were of polygonal shape and normal size. Several, small angular muscle fibers, scattered throughout the muscle, indicated a neurogenic lesion. In addition, myopathic symptoms became visible and included a few degenerating fibers and some fiber splitting.

Example 4

This example describes how mini-agrin also restored the structure of muscle basement membrane.

Mice were perfused with 2.5% glutaraldehyde in 0.1 M Na-phosphate, pH 7.4. Muscles were post-fixed overnight at 4° C. in 2.5% glutaraldehyde in 0.1 M Na-phosphate. After treatment with 1% OsO$_4$ in 0.1 M cacodylate buffer (pH 7.2), muscle pieces were rinsed in 1% Na$_2$SO$_4$ in 0.1 M cacodylate buffer and imbedded in Epon. Sixty nm-thick sections were cut on a microtome (Ultracut E, Leica), and post-stained with uranyl acetate and lead citrate. The specimens were examined with an electron microscope (Philips EM400) at an accelerating voltage of 80 kV. Pictures were taken without knowing the genotype of the mice. The mini-agrin restored the structure of muscle basement membrane ($dy^W$/mag-tg), which is disrupted (i.e., patchy) in $dy^W$ mice (Xu et al., *PNAS USA* 91: 5572–5576 (1994)) ($dy^w$), to the extent that it became indistinguishable from that of wild-type mice.

Example 5

This example compares muscle proteins in wild-type and mini-agrin-treated dystrophic mice.

The proposed molecular mechanisms that underlie the pathology of laminin α2-deficient MCMD include (1) perturbation of interactions between laminin α2 chain and its cell-surface receptors, dystroglycan and/or the integrins (Campbell. (1995), supra; Mayer (1997), supra) and (2) the failure to form a laminin-based primary scaffold necessary for basement membrane integrity. The failure to form the laminin scaffold also seems to be the reason for the muscle dystrophy in the $dy^{2J}$ mouse mutant. These mice express an amino-terminally truncated version of the laminin α2 chain that is unable to form laminin polymers in vitro but still binds to α-dystroglycan and the integrins (Colognato et al., *Curr. Biol.* 9: 1327–1330 (1999)). The muscle dystrophy in $dy^{2J}$ mutants (MacPike et al., *Proc. Soc. Exp. Biol. Med.* 151: 670–672 (1976)) is less severe than in mice that do not express the laminin-α2 chain at all, suggesting that both mechanisms contribute to the severity of the disease in $dy^W$ mutants.

To evaluate this, the expression levels of different extracellular matrix components and their cellular receptors in mice of different genotypes were measured by Western blot analysis and immunostaining. Anti-chick agrin (Gesemann (1998), supra), anti-nidogen (gift from Dr. M. Chiquet), anti-laminin α4 (Talts (2000), supra), anti-laminin α5 (Sorokin et al., *Dev. Dyn.* 210: 446–462 (1997) and a gift from Dr. R. Timpl), anti-laminin γ1 (Chemicon), anti-perlecan (Schulze et al., *Eur. J. Biochem.* 231: 551–556 (1995)), anti-α7 integrin (Mayer (1998), supra), anti-β-dystroglycan (NovoCastra), and anti-α-dystroglycan (Herrmann et al., *Hum. Mol. Genet.* 9: 2335–2340 (2000)) antibodies were used. For immunostaining, muscles were immediately immersed in OCT (Sakura Finetek) and frozen in liquid nitrogen-cooled isopentane. Frozen sections (10 μm in thickness) were incubated with blocking solution (2% horse serum, 1% BSA, 0.5% Triton X-100 in PBS) for 30 min. Primary antibodies were diluted in incubation buffer (2% horse serum, 1% BSA, 0.01% Triton X-100 in PBS) and incubated overnight at 4° C. Sections were washed 4 times with incubation buffer and appropriate secondary antibodies were incubated at room temperature for 2 hr. To determine protein expression levels, the primary antibodies were diluted such that the signal was not saturated. Images were collected and analyzed with a confocal microscope (Leica TCS-8P) and appropriate software. The microscope was calibrated using the InSpeck Microscope Image Intensity Calibration Kit (Molecular Probes). Specific intensity was calculated for each image as the signal intensity of the muscle circumference minus that of an adjacent, non-stained region (Turney et al., *J. Neurosci. Methods* 64: 199–208 (1996)). Five different pictures were taken using the same parameters on each section and 4 different sections were used for each individual mouse.

No changes were detected in the amounts of the extracellular matrix protein perlecan, nidogen and the laminin γ1 chain (Table 1). Similarly, the levels of α7β1 integrin, the main integrin receptor of laminin-2 and laminin-4, remained unchanged in all genotypes (Table 1). In contrast, significant alterations were observed for the laminin α4 and α5 chains (Table 1). In wild-type animals, both α chains of laminin were mainly concentrated around blood vessels and only little immunoreactivity was associated with muscle basement membrane. In agreement with others (Patton (1997), supra; Ringelmann (1999), supra), the amount of basement membrane-associated laminin α4 was strongly increased in dy$^W$ mice, but was not further influenced by the mini-agrin (Table 1). In strong contrast, the amount of the α5 chain was strongly influenced by mini-agrin (Table 1). Interestingly, only a slight increase in the amount of the laminin α5 chain was observed in two mag-tg mice on wild-type background (animal 1: 123±5%; animal 2: 164±11%). Thus, mini-agrin-induced upregulation of the laminin α5 chain is also dependent on the genetic background of the mice.

Examination of α- and β-dystroglycan revealed that the two proteins were regulated differentially. This is particularly interesting as both proteins are derived from a single transcript and are generated by post-translational mechanisms (Ibraghimov-Beskrovnaya et al., Nature 355: 696–702 (1992)). The amount of the transmembrane component, β-dystroglycan, was approximately 3 times higher in both dy$^W$ and dy$^W$/mag-tg mice (Table 1). Despite the increase in β-dystroglycan, the amount of α-dystroglycan was decreased in the dy$^W$ mice (Table 1). Expression of mini-agrin, which binds to α-dystroglycan, restored the amount of α-dystroglycan in dy$^W$/mag-tg mice to almost wild-type level (Table 1). The change in the expression of α- and β-dystroglycan was again dependent on the genetic background as their levels in mag-tg mice were not different from wild-type mice. The increase in the amount of α-dystroglycan and the laminin α5 chain in dy$^W$/mag-tg mice does not involve upregulation of gene transcription, as determined by RT-PCR. Thus, the binding of mini-agrin to α-dystroglycan and α5 chain-containing laminins stabilizes them.

To further investigate this, Sepharose beads coupled to wheat-germ lectin (WGL) were used, which bind to α-dystroglycan (Ervasti et al., J. Biol. Chem. 266: 9161–9165 (1991)) but not to the mini-agrin protein, to enrich α-dystroglycan from skeletal muscle extracts. Muscles were homogenized in 500 μl incubation buffer (50 mM Tris-HCl, pH 7.5, 0.2 M NaCl, 1.25 mM CaCl$_2$, 1 mM MgCl$_2$). After centrifugation at 20,000 g, the supernatant was collected and the pellet was re-extracted with 1% Triton X-100 in incubation buffer for 30 min on ice. After centrifugation at 20,000 g, the supernatant was collected and pooled with the supernatant from the first centrifugation. WGL Sepharose beads (100 μl; Amersham Pharmacia) were added and incubated for 2 hr at 4° C. WGL-beads were washed 4 times with incubation buffer, and proteins were eluted in 75 mM Tris-HCl, pH 6.8, 3.8% SDS, 4 M urea, 20% glycerol, and 5% β-mercaptoethanol. Proteins were separated on a 3–12% SDS-PAGE, and immunoblotted using anti-chick agrin antibodies. The mini-agrin protein co-precipitated with WGL-Sepharose, indicating that α-dystroglycan and the mini-agrin protein form a protein complex. The co-precipitation was specific as no enrichment of the mini-agrin protein was detected when muscle extracts from mag-tg mice were treated with non-conjugated Sepharose beads.

TABLE 1

Amount of protein detected in the different genotypes

| Protein | dy$^W$ | | | dy$^W$/mag-tg | | |
|---|---|---|---|---|---|---|
| | Confocal microscopy | | Western-blot | Confocal microscopy | | Western-blot |
| perlecan | 106 ± 25 | 94 ± 23 | 110 ± 30 | 115 ± 17 | 108 ± 13 | 180 ± 30 |
| Laminin γ1 | 107 ± 27 | 104 ± 13 | n.d. | 117 ± 26 | 110 ± 14 | n.d. |
| nidogen | n.d. | n.d. | 70 ± 10 | n.d. | n.d. | 90 |
| Laminin α4 | 970 ± 100* | 1480 ± 200* | 320 ± 110 | 1090 ± 170* | 1810 ± 260*† | 410 ± 30 |
| Laminin α5 | 147 ± 29* | 170 ± 40* | 126 ± 72 | 440 ± 68*† | 636 ± 79*† | 371 ± 130 |
| α 7-integrin | 157 ± 38* | 100 ± 20 | 80 ± 20 | 181 ± 61 | 104 ± 28 | 90 ± 4 |
| α-dystroglycan | 33 ± 7* | 22 ± 5* | n.a. | 86 ± 14† | 86 ± 15† | n.a. |
| β-dystroglycan | 300 ± 77* | 240 ± 30* | 250 ± 90 | 350 ± 76* | 250 ± 34* | 200 ± 90 |

Values are expressed as percentage of the levels found in wild-type mice (normalized to 100%). In confocal microscopy measurements, two series of experiments are represented; the values are the mean±standard error N=20). For immunoblotting experiments (Western-blot), data from 2 to 5 different mice were pooled and the values given represent the mean±standard deviation. Because the values of the confocal microscopy measurement are not normally distributed, statistical analysis was performed with each series separately. Values significantly different from wild-type mice are indicated by asterisk (*; Wilcoxon test p<0.001). Values significantly different from dy$^W$ mice are indicated by a cross (†; Wilcoxon test p<0.001). Because of the low number of samples and non-normal distribution, data from Western-blot were not subjected to statistical analysis. n.a.: not applicable; n.d.: not determined.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the claims.

What is claimed is:

1. A method of treating congenital muscular dystrophy due to a mutation in the LAMA2 gene in a mammal, said method comprising administering to the mammal (a) a therapeutically effective amount of a protein or polypeptide comprising (i) at least one binding domain for a laminin, (ii) at least one binding domain for α-dystroglycan, and (iii) at least one follastatin-like domain, or (b) a nucleic acid molecule encoding the protein or polypeptide, wherein the at least one binding domain for a laminin, the at least one binding domain for α-dystroglycan, and the at least one follastatin-like domain are from agrin, whereupon the mammal is treated for congenital muscular dystrophy.

2. The method of claim 1, wherein the protein or polypeptide is administered by intramuscular injection.

3. The method of claim 1, wherein a nucleic acid molecule encoding the protein or polypeptide is administered to the mammal, whereupon the nucleic acid molecule is expressed in the mammal and the protein or polypeptide is produced.

4. The method of claim 3, wherein the nucleic acid molecule is administered by intramuscular injection.

5. The method of claim 3, wherein the nucleic acid is in the form of a viral vector.

6. The method of claim 5, wherein the viral vector is selected from the group consisting of an adenoviral vector, an adeno-associated viral vector, a retroviral vector, a Herpes simplex viral vector, a lentiviral vector, a Sindbis viral vector, or a Semliki forest viral vector.

7. The method of claim 3, wherein the nucleic acid molecule is operably linked to a promoter selected from the group consisting of a muscle creatine kinase (MCK) promoter, a cytomegalovirus (CMV) promoter, a tetracycline-regulatable promoter, and a doxycycline-regulatable promoter.

8. The method of claim 1, wherein the mammal is a human.

* * * * *